United States Patent
Joseph et al.

(10) Patent No.: US 9,625,291 B1
(45) Date of Patent: Apr. 18, 2017

(54) DETERMINING EQUIPMENT THROUGHPUT AND SPARE CAPACITY CHARACTERISTICS OF A SERVICE FACILITY WITHOUT DIRECT OBSERVATION

(71) Applicant: Visiun, Inc., Ann Arbor, MI (US)

(72) Inventors: Thomas Paul Joseph, Ann Arbor, MI (US); Denis Robert Burke, Canton, MI (US)

(73) Assignee: VISIUN, INC., Ann Arbor, MI (US)

( * ) Notice: Subject to any disclaimer, the term of this patent is extended or adjusted under 35 U.S.C. 154(b) by 800 days.

(21) Appl. No.: 14/055,748

(22) Filed: Oct. 16, 2013

(51) Int. Cl.
*G01D 21/00* (2006.01)

(52) U.S. Cl.
CPC .................... *G01D 21/00* (2013.01)

(58) Field of Classification Search
USPC ........................................................ 702/182
See application file for complete search history.

(56) References Cited

U.S. PATENT DOCUMENTS

2008/0112321 A1* 5/2008 Ricketts ............... G06Q 10/087
370/235

* cited by examiner

*Primary Examiner* — Tung Lau
(74) *Attorney, Agent, or Firm* — Hickman Palermo Becker Bingham, LLP

(57) ABSTRACT

In an embodiment, a method comprises: retrieving, without direct observation, one or more activity measures recorded within a particular time period and associated with activities performed by a group of analyzers in a specimen analysis laboratory; transforming the activity measures into a count of activities performed by the group of analyzers within the particular time period; determining whether the count of activities for the group of analyzers is less than a peak value for the group of analyzers; in response to determining that the count of activities for the group of analyzers is less than a peak value: determining a spare capacity value for the group of analyzers for the particular time period as a difference between the peak value and the count of activities for the group of analyzers; causing generating a first display of the spare capacity value for the group of analyzers on a computer display unit.

20 Claims, 7 Drawing Sheets

| Wrkstn | VerDate | VerHr | Accn | TestID | Inst, Accession, Test |
|---|---|---|---|---|---|
| LH1 | 06/24/2010 | 7 | U1126344 | ABC | Inst 1, Accn 1, Test 1 |
| LH1 | 06/24/2010 | 7 | U1126344 | ADIFF | Inst 1, Accn 1, Test 2 |
| LH1 | 06/24/2010 | 7 | U1126354 | ABC | Inst 1, Accn 2, Test 1 |
| LH1 | 06/24/2010 | 7 | U1126354 | ADIFF | Inst 1, Accn 2, Test 2 |
| LH2 | 06/24/2010 | 7 | U1126394 | ABC | Inst 2, Accn 3, Test 1 |
| LH2 | 06/24/2010 | 7 | U1126394 | ADIFF | Inst 2, Accn 3, Test 2 |
| LH2 | 06/24/2010 | 7 | U1126414 | ABC | Inst 2, Accn 4, Test 1 |
| LH2 | 06/24/2010 | 7 | U1126443 | ABC | Inst 2, Accn 5, Test 1 |
| LH2 | 06/24/2010 | 7 | U1126443 | ADIFF | Inst 2, Accn 5, Test 2 |
| RXL1 | 06/24/2010 | 7 | X1128735 | UALB | Inst 3, Accn 6, Test 3 |
| RXL1 | 06/24/2010 | 7 | E1133171 | UALB | Inst 3, Accn 7, Test 3 |
| RXL2 | 06/24/2010 | 7 | E1133493 | BHCG | Inst 4, Accn 8, Test 4 |
| RXL2 | 06/24/2010 | 7 | E1136840 | NTBNP | Inst 4, Accn 9, Test 5 |
| RXL3 | 06/24/2010 | 7 | U1125766 | METB | Inst 5, Accn 10, Test 6 |
| RXL3 | 06/24/2010 | 7 | U1125773 | METB | Inst 5, Accn 11, Test 6 |
| RXL3 | 06/24/2010 | 7 | U1125778 | METB | Inst 5, Accn 12, Test 6 |
| RXL3 | 06/24/2010 | 7 | U1125778 | MGN | Inst 5, Accn 12, Test 7 |
| RXL3 | 06/24/2010 | 7 | U1125782 | METC | Inst 5, Accn 13, Test 8 |
| RXL3 | 06/24/2010 | 7 | U1125804 | AMY | Inst 5, Accn 14, Test 9 |
| RXL3 | 06/24/2010 | 7 | U1125804 | HFP | Inst 5, Accn 14, Test 10 |
| RXL3 | 06/24/2010 | 7 | U1125804 | MGN | Inst 5, Accn 14, Test 11 |
| RXL3 | 06/24/2010 | 7 | U1125804 | PHOS | Inst 5, Accn 14, Test 12 |

Fig. 2

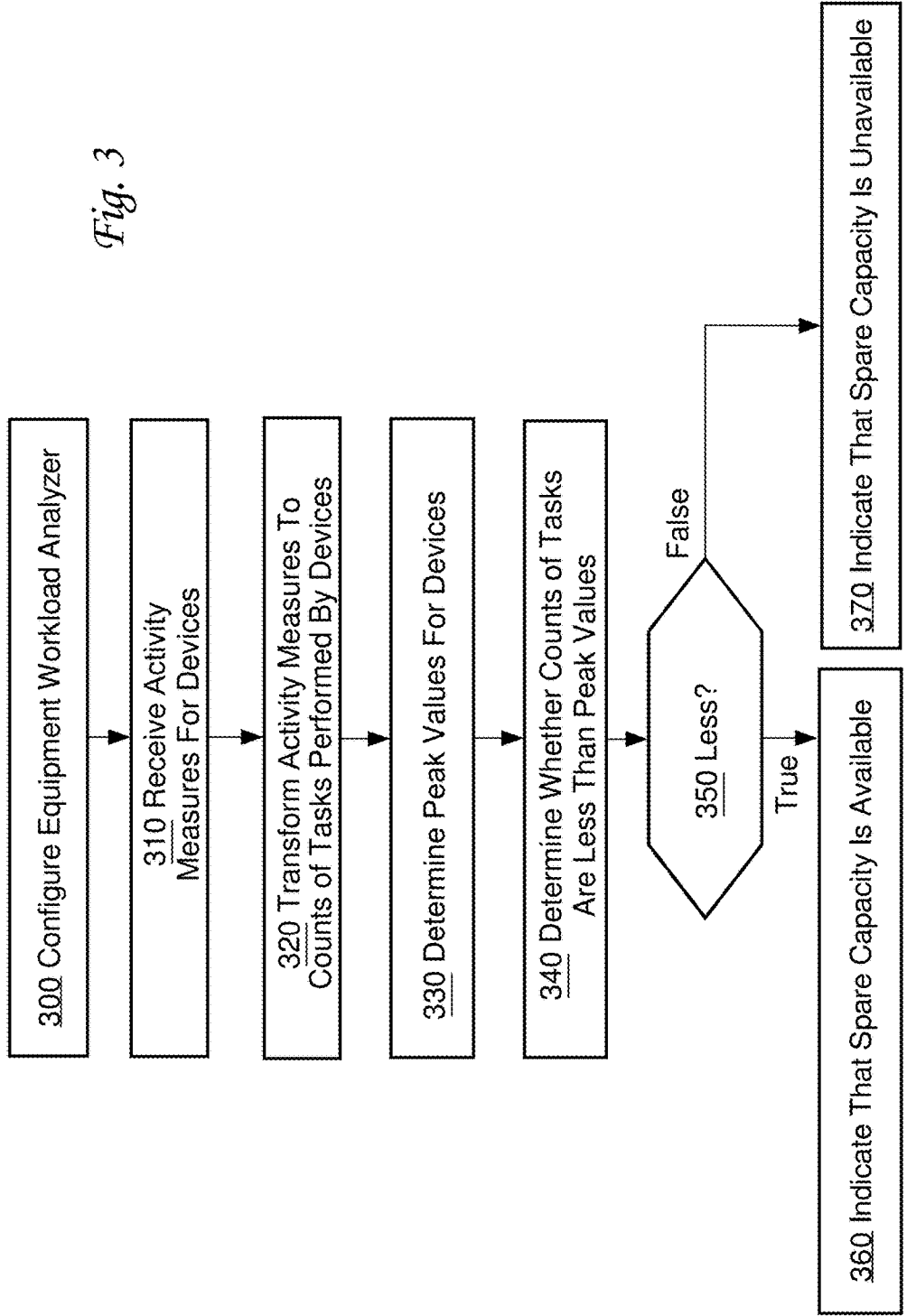

DETERMINING EQUIPMENT THROUGHPUT AND SPARE CAPACITY CHARACTERISTICS OF A SERVICE FACILITY WITHOUT DIRECT OBSERVATION

TECHNICAL FIELD

The present disclosure is generally related to data benchmarking for purposes of evaluating performance of service facilities, and more specifically, to computer-implemented processes for determining equipment throughput, spare capacity characteristics and related metrics for a service facility.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

An objective in service monitoring is to determine whether the equipment used at a service facility is efficiently utilized. Equipment throughput monitoring may be especially important in facilities that have deployed equipment or devices that are expensive and unique. Such facilities may include medical clinics and laboratories that operate expensive chemistry, hematology, molecular or other analyzers, mass spectroscopes, computer-tomography scanners, and the like. The capital cost of such equipment may motivate maximal use of the equipment to defray its costs; further, some equipment may achieve operational cost efficiency only through continuous or regular use. Monitoring of the activities performed by such devices may help in generating data for optimizing throughput of the devices and determining whether any of the devices has any spare capacity. In particular, the monitoring may help in identifying time periods during which some of the devices are underutilized.

Equipment throughput in a service facility may be determined by visual monitoring of the equipment and recording information about the workload levels of the devices. However, in some situations, the information obtained via manual visual monitoring may be incomplete or insufficient to determine the actual throughput or the actual spare capacity characteristics of the devices. For example, visually determined and manually recorded information may fail to accurately itemize some of the activities, or the exact time periods during which some activities take place. Also, some counts of the activities, in certain patient types, may not be reflected in the visually determined and manually recorded workload information. However, if such services significantly impact the workload of the devices, but information about them is unavailable, then determining the equipment throughput and spare capacity accurately may be difficult.

SUMMARY OF THE INVENTION

The appended claims may serve as a summary of the invention.

BRIEF DESCRIPTION OF THE DRAWINGS

In the drawings:

FIG. 2 illustrates an embodiment of data records maintained by a computer information system;

FIG. 3 illustrates an embodiment of a process for determining equipment throughput and spare capacity characteristics of a service facility;

DESCRIPTION OF EXAMPLE EMBODIMENTS

Figure 1:
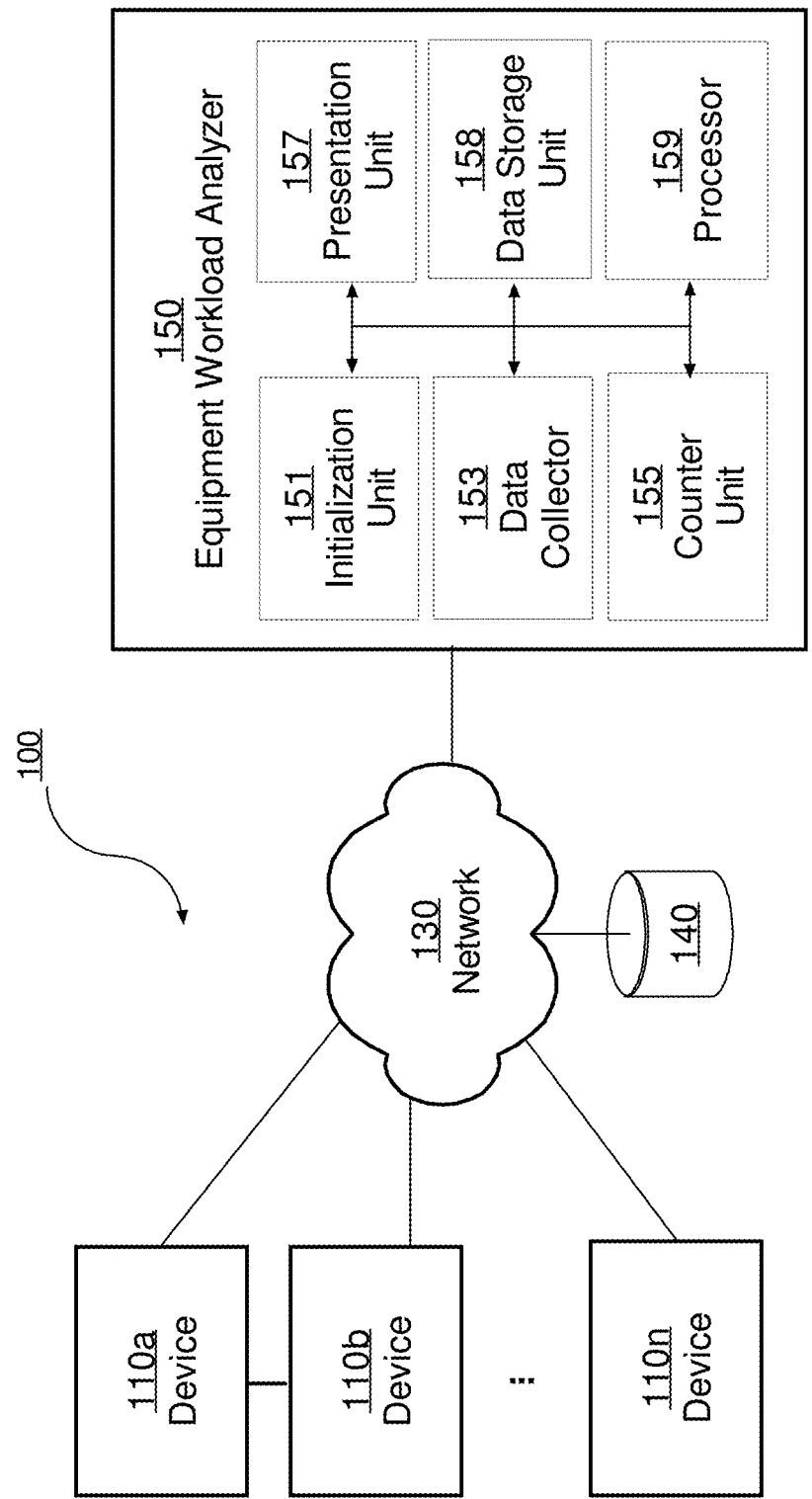
FIG. 1 illustrates an embodiment of a system configured to determine equipment throughput and spare capacity characteristics of a service facility.

In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Embodiments are described herein according to the following outline:

1.0 Overview
2.0 Structural and Functional Overview
3.0 Types of Activity Measurements
4.0 Determining Equipment Throughput and Spare Capacity Characteristics
5.0 Types of Reports
6.0 Examples of Reports
7.0 Implementation Mechanisms—Hardware Overview
8.0 Extensions and Alternatives

1.0 Overview

The various embodiments of the present disclosure address the above-described challenges with important improvements over the prior art in terms of determining equipment throughput and spare capacity characteristics of a service facility. For purposes of illustrating clear examples, certain embodiments described below refer to a service facility in terms of medical applications. However, the described approaches may be implemented in any type of service facility, not necessarily medical facilities. For example, the approaches may be implemented in retail applications or any other service-providing applications.

In an embodiment, a process of determining equipment throughput and spare capacity characteristics of a service facility is performed by one or more of special-purpose computers, arrangements of computer-executable instructions for use with general-purpose computers, or other computer-implemented processes. Thus, the disclosure is intended to be directed to practical applications of the techniques herein to computer implementations that operate upon data gathered from tangible, real-world service facilities.

In an embodiment, an approach provides a computer-implemented process configured to determine detailed information about activities performed by various devices providing services at a service facility, and use the detailed information to determine equipment throughput and spare capacity characteristics of the facility.

Detailed information about the activities may be obtained in a variety of ways. For example, some of the information may be accessed from a computer information system maintained by the service facility. The information may be manually entered into the information system or automatically downloaded from a variety of workstations, sensors and computer devices.

In an embodiment, in medical laboratory applications, information about activities related to providing services at a laboratory may be retrieved from a laboratory information system (LIS) maintained by the laboratory. The retrieved information may include for example, encoded information about the tests performed by various workstations and analyzers at the laboratory.

In an embodiment, sets of information about activities performed at a service laboratory are referred to as activity measures. In medical applications, activity measures may be obtained for various activities performed by various pieces of medical equipment, such as hematology analyzers, and the like. The embodiments allow counting various types of activities, and provide quite precise activity measures for the equipment. Therefore, equipment throughput and spare capability characteristics generated from the activity measures may be determined with a high level of accuracy.

In an embodiment, an approach comprises retrieving one or more activity measures recorded within a particular time period and associated with activities performed by a group of devices in a service facility. The activity measures may be received from a variety of sources, including an activity log of a laboratory information system. The activity measures are used to determine equipment throughput and spare capacity characteristics.

The types of activity measures may depend on the implementation. For example, in medical applications, the activity measures may pertain to the measures of any one of: processing a patient collection, processing a specimen or container, performing a test on the specimen, or obtaining results for the test performed on the specimen accession.

One or more activity measures may be transformed into a count of activities performed by the group of devices within the particular time period, and a determination may be made whether the count of activities for the group is less than a peak value for the group.

In response to determining that a count of activities for the group of devices is less than the peak value for the group, a spare capacity value for the group for a particular time period is determined. The spare capacity value may be determined as a difference between the peak value and the count of activities for the group.

In an embodiment, a first display of the spare capacity value for the group of devices on a computer display unit is generated.

In an embodiment, transforming the one or more activity measures comprises incrementing the count of activities for each instance of an activity measure, of the activity measures, that has been recorded in a computer information system for any device of the group within the particular time period.

In an embodiment, one or more activity measures are transformed into one or more individual counts of activities performed by one or more devices of the group of devices within the particular time period. For each individual count of activities, a determination is made whether the individual count of activities for the device is less than an individual peak value for the device.

If the individual count of activities for a device is less than an individual peak value for the device, then, an individual spare capacity value for the device for the particular time period is determined as a change between the individual peak value for the device and the individual count of activities for the device.

In an embodiment, a second display of the individual spare capacity value for the device is generated on the computer display unit.

In an embodiment, the transforming the one or more activity measures comprises incrementing, for each device, the individual count of activities for each instance of a activity measure, of the activity measures, that has been recorded in a laboratory information system for the device of the group of devices within the particular time period.

In an embodiment, an approach comprises determining, based on the one or more individual counts determined for the one or more devices, which of the one or more devices performs at a peak capacity during the particular time period.

In an embodiment, an approach comprises determining, based on the one or more individual counts determined for the one or more devices, a particular time sub-period, within the particular time period, at which one or more of the group of devices performs at a peak capacity.

In an embodiment, a graphical user interface (GUI) is generated and displayed on a computer display. The GUI may provide an indication of whether a spare capacity for a group of devices or an individual device is available.

In an embodiment, an electronic message is generated. The electronic message may indicate whether spare capacity for an individual device or a group of devices is available. The message may be sent to one or more users.

In an embodiment, indications of the following are generated: activity throughput data for each device of the group of devices, peak throughput data for an individual device, and an available capacity value for the group of devices.

In an embodiment, the method is performed by one or more computing devices. Various embodiments include computer-implemented methods performed by executing sequences of program instructions that embody the methods using a general-purpose computer; special-purpose computers that comprise logic or are programmed with instructions which when executed cause performing the methods; and computer program products and/or tangible, non-transitory computer-readable storage media storing sequences of instructions which when executed cause performing the methods.

The foregoing and other features and aspects of the disclosure will become more readily apparent from the following detailed description of various embodiments.

2.0 Structural and Functional Overview

In an embodiment, a computer-implemented process, computer system and computer program are provided for determining equipment throughput and spare capacity characteristics of a service facility. The system described herein may be implemented in any type of a customer service facility or a service provider facility. For example, the system may be implemented in medical facilities, including medical laboratories, clinics, hospitals, physician offices, as well as other facilities providing services to customers.

FIG. 1 illustrates an embodiment of a system configured to determine equipment throughput and spare capacity characteristics of a service facility. In an embodiment, computer system 100 comprises one or more pieces of equipment (devices) 110*a*, 110*b*, 110*n*, one or more networks 130, one or more system databases 140, and one or more equipment workload analyzers 150. For the purpose of illustrating clear examples, FIG. 1 shows three devices 110*a*, 110*b*, 110*n*;

however, other embodiments may use any number of devices as suggested by the ellipsis between stations 110b, 110n.

In an embodiment, devices 110a, 110b, 110n represent various pieces of equipment configured to process data. In medical applications, devices 110a, 110b, 110n may correspond to various types of medical instruments, such as chemistry analyzers, hematology analyzers, urine analyzers, DNA analyzers, and the like. Examples of chemistry analyzers include the Beckman Coulter UniCel® DxC 600 Synchron Clinical System and the Beckman Coulter AU480 Chemistry System. Examples of hematology analyzers include the COULTER® LH 780 and the COULTER® HmX Hematology Analyzer. Devices 110a, 110b, 110n may also correspond to other types of devices, including sterilizers, autoclaves, defibrillators, bone densitometers, body composition analyzers and the like.

In an embodiment, in copy-center applications, devices 110a, 110b, 110n represent various pieces of equipment configured to provide copying, scanning, printing and faxing services. For example, devices 110a, 110b, 110n may correspond to copy machines, fax machines, printers, scanners, multi-function printing devices (MFP), and the like.

Devices 110a, 110b, 110n may be configured to perform various activities, generate output data and transmit the output data to database 140 and an equipment workload analyzer 150. The output data may be transmitted via network 130 (as depicted in FIG. 1) or directly to database 140 and equipment workload analyzer 150. For example, a device 110a may be a blood analyzer configured to receive blood specimen as input data, process the blood specimen to generate test results, transmit the test results via network 130 to database 140, or directly to equipment workload analyzer 150.

Devices 110a, 110b, 110n may be operated by technicians and data processing employees. For example, if a device 110a is a blood analyzer, then device 110a may be operated by a technician who places specimens on the analyzer, and starts an analysis process on the analyzer. Once the analysis is finished, the technician may remove the specimens from the analyzer and use an interface implemented on the analyzer 110a to enter data into a LIS. In some cases the test results are sent to the LIS without technologist intervention (termed autovalidation, based on certain rules), in other cases the technologist reviews the results and approved them for reporting, using the LIS or middleware to review the results. In either case, the entered data may comprise details about the tests performed by the analyzer, and may be used to determine workload characteristics of the analyzer.

In an embodiment, if a device 110b is a copy machine, then device 110b may be operated by a technician who places a copy job in the feeding slot of the copy machine, enters copying settings (a count of copies, a type of paper, double-sided or single sided, and the like) using a user interface of the copy machine, and starts the copy process. Once the copying is finished, the technician may remove the originals and copies from the machine, and use the interface to enter data into a copy-center information system. The entered data may comprise details about the jobs performed by the copying machine, and may be used in determining workload characteristics of the analyzer.

Devices 110a, 110b, 110n may be configured with a user interface for entering data, requesting various types of outputs, and requesting data transfer to other stations or computer workstations. For example, device 110a may be configured with a user interface for facilitating data transfer from the devices to a computer workstation located at a nursing station.

Devices 110a, 110b, 110n may also be configured to provide information about workload and throughput characteristics of the devices. For example, a device 110n may be configured to generate the workload and throughput characteristics for a particular time period, or to provide reports summarizing workload and throughput characteristics of the device 110n during various time periods.

Devices 110a, 110b, 110n may also be configured as workstations capable of performing various activities and services. For example, a device 110a may be a PC-based electrocardiogram (ECG) device, configured to measure electrical activity of the heart over a period of time, and display the measurement results on a display of the device 110a. A workstation may be any type of a computing device, including workstations, laptops, PDA devices, smartphones, tablet devices or any other computer devices configured to receive, process, and transmit data.

Database 140 may be any type of a process, system or device configured to receive, store and transmit data. Examples of such devices include flat files, distributed storage, relational databases, or any other data repository. Data entered into database 140 may be managed by an information system hosted or executing using another computer. For example, in case of medical applications, data entered into database system 140 may be managed by a LIS.

Data entered into database 140 may be represented in a variety of data structures. For example, the data may be stored as representing spreadsheets, tables, lists, data objects, and any other data structures.

Data entered into database 140 may be entered in a variety of ways. The data may be entered manually, automatically or partially manually and partially automatically. For example, the data may be manually entered by a staff employee who types the information on a keyboard of a workstation or device 110a. The data may be also entered by scanning a bar code or a quick response (QR) code image using a scanner, and transmitting the scanned data to database 140. The data may also be automatically downloaded from or by devices 110a, 110b, 110n.

Network 130 facilitates communications between devices 110a, 110b, 110n, database 140 and equipment workload analyzer 150. For example, network 130 may be configured to receive information from devices 110a, 110b, 110n, store the received information in database 140, transmit the information from database 140 to equipment workload analyzer 150 and receive the information from equipment workload analyzer 150.

Equipment workload analyzer 150 may be configured to request, receive, process, and analyze data reflecting workload and throughput characteristics of computer system 100. Equipment workload analyzer 150 may receive data directly or indirectly from devices 110a, 110b, 110n. Equipment workload analyzer 150 may also receive data directly or indirectly from network 130, and other sources (not depicted in FIG. 1).

Configurations of an equipment workload analyzer 150 may vary in different implementations, and the types and quantity of components implemented within the equipment workload analyzer 150 may depend on the type of the service facility.

In an embodiment, an equipment workload analyzer 150 comprises one or more initialization units 151, one or more data collectors 153, one or more counter units 151, one or more data collectors 153, one or more counter units 155, one or more presentation units 157, one or more data storage units 158, and one or more processors 159. In other embodiments, one of each type of the units 151-159 may be present. For example, as depicted in FIG. 1, equipment workload analyzer 150 may comprise one initialization unit 151, one data collector 153, one counter unit 151, one data collector 153, one counter unit 155, one presentation unit 157, one data storage unit 158, and one processor 159. In other embodiments, the functionalities of units 151-159 may be combined and the quantity of various types of the units may be reduced.

In an embodiment, each of the processes described in connection with the functional blocks of FIG. 1 may be implemented using one or more computer programs, other software elements, and/or digital logic in any of a general-purpose computer or a special-purpose computer, while performing data retrieval, transformation and storage operations that involve interacting with and transforming the physical state of memory of the computer. Or, equipment workload analyzer 150 may implement the processes described herein using hardware logic such as in an application-specific integrated circuit (ASIC), field-programmable gate array (FPGA), system-on-a-chip (SoC) or other combinations of hardware, firmware and/or software.

Initialization unit 151 may be configured to initialize a process of determining equipment throughput and spare capacity characteristics of a service facility. For example, initialization unit 151 may be configured to receive data from various computer information systems, determine various types of devices that provide services, determine one or more groups for the various types of devices, and determine sources of information providing data for determining throughput characteristics of the devices.

Initialization unit 151 may also be configured to determine time periods for which the throughput characteristics are sought. Moreover, initialization unit 151 may be configured to determine various methods for identifying different activities from data provided by computer information systems, and various types of reports that may be generated by equipment workload analyzer 150.

Data collector 153 may be configured to request and receive data reflecting activity measures for various activities performed by devices 110*a*, 110*b*, 110*n*. The data may be collected for specified time periods and for specified time intervals. For example, in medical applications, the collected data may represent activity measures for the activities performed by devices 110*a*, 110*b*, 110*n*. The activity measures may be collected during certain times of a day, certain days, certain weeks and time periods.

Examples of activity measures collected by data collector 153 include information about the activities performed by devices 110*a*, 110*b*, 110*n*. The activity measures may also include information about devices 110*a*, 110*b*, 110*n* that performed the activities, time and day information associated with performing the activities, and other service-related information. For example, in medical applications, the activity measures collected by data collector 153 may include information indicating unique identifiers of accessions and collections of specimens loaded to and processed by a hematology analyzer. In copy-center applications, the activity measures collected by data collector 153 may include information indicating counts of copy-jobs sent to a copy machine, a count of copies that have been requested, information indicating special surcharges added to the copy job due to the special processing of the copies, and the like. Upon receiving the activity measures, data collector 153 may transmit the measures to a counter unit 155.

Counter unit 155 may be configured to receive activity measures collected by data collector 153. Counter unit 155 may also be configured to process the received data to determine various characteristics of devices providing services to customers or clients in system 100. For example, counter unit 155 may be configured to determine counts of various activities performed by the devices, throughput characteristics of the groups of devices and characteristics of individual devices, and whether any of the devices or groups has some spare capacity.

In an embodiment, upon receiving activity measures for tests performed by one or more hematology analyzers, counter unit 155 may determine counts for the tests performed by each of the analyzers, use the counts to determine throughput characteristics for each of the analyzers, and determine whether any of the analyzers has some spare capacity. This may be illustrated using the following example: if counter unit 155 received information indicating that system 100 deployed three hematology analyzers LH1, LH2 and LH3, and the maximum number of specimens that each individual analyzer may process is 118, but during a particular time interval, the analyzers actually processed 118, 11 and 0 specimens, respectively, then the spare capacity of the group may be determined as a difference between the total maximum number of specimens that the analyzers could have processed during the particular time interval and the total actual number of specimens that the analyzers actually processed. The difference may be expressed as follows: (118*3)−(118+11+0)=354−129=225. The spare capacity characteristics of the group of the analyzers indicate that the analyzers had the ability to process additional 225 specimens during the particular time interval.

Presentation unit 157 may be configured to output throughput and spare capacity characteristics generated by counter unit 155. Throughput characteristics may indicate fluctuations of throughput levels within a day, a work week, a month, or a year. For example, throughput characteristics may indicate counts of paper copies that a copy machine generated within a particular time period, such as a day, a week, and so forth. Spare capacity characteristics may indicate whether the devices have any capabilities to perform additional activities. For example, spare characteristics may indicate counts of additional accessions or containers of specimens that each of the analyzers could have tested during a particular time period.

In an embodiment, throughput and spare capacity characteristics may be provided to a user in a form of a report. A report may include spreadsheets, charts, graphs, plots and outliers. The reports may be printed as hard copies or displayed on displays of computing devices. The reports may be graphically displayed as part of a graphical user interface (GUI), a graphical dashboard, a computer-navigated chart, or any other computer generated graphical depiction.

Reports may indicate time periods during which the devices were working at the full capacity, and time periods during which devices had some spare capacity. The reports may also indicate the time periods during which the throughput levels were higher than average or lower than average. Further, the reports may provide suggestions as to how the throughput issues may be resolved.

Data storage 158 may be configured to store a variety of data, including activity measures for various activities performed by devices of system 100, throughput characteristics of the devices, spare capacity characteristics of the devices, reports and other types of information. Data storage 158 may be implemented in one or more storage devices communicatively coupled with each other and managed locally or globally.

Processor 159 executes commands and instructions specific to equipment workload analyzer 150. For example, processor 159 may facilitate communications to and from equipment workload analyzer 150, process commands, process responses, and facilitate various types of operations executed by equipment workload analyzer 150. Processor 159 may comprise hardware and software logic configured to execute various processes on equipment workload analyzer 150.

3.0 Types of Activity Measurements

In an embodiment, equipment throughput and spare capacity characteristics of a service facility are determined based, at least in part, on measures of activities performed by the equipment deployed by the service facility. The types of activities may depend on the type of the service facility. For example, if the service facility is a medical laboratory, then examples of activities may include performing tests on specimens, accessions, and containers of specimens obtained from patients. Collecting specimens from a patient is referred to as a patient collection. An accession is a unique identifier that for a set of tests from a single patient applied to one or more containers filled with the specimen. A container is an individual tube or cup containing specimens. Knowing the activity measures of the tests and the counts of each of the activity measures may allow determining equipment throughput and spare capacity characteristics of the facility.

In an embodiment, information about activity measures processed by devices deployed by a service facility may be collected, stored and maintained by a LIS. However, in some implementations, the information stored in a LIS may be incomplete. For example, some LIS systems may fail to store the information directly indicating a count of tests that each of the devices performed. Some LIS systems may capture information about some tests, but not all tests. For example, a LIS implemented in a medical laboratory may be configured to capture information about the tests performed on entire containers of accessions containing specimens obtained from the patients; however, it may not directly indicate the counts of different tests, or the counts of accessions in each of the collections. Therefore, in some contexts, the LIS may be unable to directly provide information about all tests, all collections, accessions, and the like.

However, in some situations, incomplete information about activities performed by devices deployed by a service facility may be processed, and the detailed information about the activities may be determined. The particular methods for deriving such data may vary and depend on the implementation of a LIS. An example of one such method is described in FIG. 2.

FIG. 2 illustrates an embodiment of data records maintained by a computer information system. In the depicted example, the data records are typical to medical applications; however, similar records may be generated by a LIS maintained by other service facilities. The information depicted in FIG. 2 does not correspond to any actual data collected and maintained for actual patients. FIG. 2 depicts a screen snapshot of data that was generated merely for the purpose of illustrating clear examples and is not specific to any particular medical facility or any particular patient.

Data records maintained by a LIS may be stored in a variety of data structures, including tables, lists, data objects, and the like. In the example depicted in FIG. 2, data records are organized in a table that has rows and columns. The rows contain individual data entries, and an entry is used to store information about an activity performed by a device.

An entry in a LIS may include encoded information about an activity performed by a device deployed in a service facility. For example, a LIS may have entries indicating tests performed by analyzers and other devices. The information may be processed to determine counts of the activities.

Columns in the table of FIG. 2 are labeled for a workstation identifier 250, verification date 252, a verification time 254, an accession identifier 256, a test identifier 258, and a description 260, including the instrument identifier, accession identifier and test identifier.

The table depicted in FIG. 2 comprises data for five different devices: two Beckman Coulter® LH Hematology Analyzer hematology analyzers LH1 and LH2, and three Siemens Dade Behring Dimension RxL® chemistry analyzers RX1, RX2 and RX3. Data entries for LH1 are described in detail below.

In FIG. 2, rows 210-216 store information about the tests performed on LH1 on Jun. 24, 2010 (as indicated in column 252) at 7 AM (as indicated in column 254). The table indicates two types of tests performed on LH1 at that time. The types include ABC and ADIFF. Column 256 indicates that two accessions were used to perform each test on LH1. In particular, the tests ABC and ADIFF were performed on the accession identified as U1126344, and the tests ABC and ADIFF were performed on the accession identified as U1126354. Based on that information, it may be inferred that on Jun. 24, 2010 at 7 AM four tests were performed on LH1. This determination is more accurate than relying just on the count of accessions or relying just on the count of different tests performed on the LH1.

The above described approach for determining a count of tests performed on a LH1 analyzer may also be used to determine the counts of tests performed on each of the remaining devices listed in FIG. 2. In particular, FIG. 2 shows that, on the particular day and at the particular time, five tests were performed on LH2, two tests were performed on RXL1, two tests were performed on RXL2, and nine tests were performed on RXL3. The counts of tests performed on the devices may be used to determine workload characteristics and spare capacity characteristics for the devices.

4.0 Determining Equipment Throughput and Spare Capacity Characteristics

FIG. 3 illustrates an embodiment of a process for determining equipment throughput and spare capacity characteristics of a service facility. The process is directed to collecting detailed information about various activities performed by devices deployed by a service facility and facilitating providing services to users. The detailed information is used to generate relatively accurate equipment throughput and spare characteristics of the facility.

In step 300, an equipment workload analyzer is configured. Configuring an equipment workload analyzer may include determining the types of devices deployed in the facility and how the devices may be grouped, the types of activities that the devices perform, the time periods for which the characteristics may be determined, and the sources for providing information about the activities performed by the devices.

Specific activities involved in configuring an equipment workload analyzer usually depend on the type of the service facility and the type of services that the facility provides. For example, if the process is implemented in a copy-processing center, then configuring an equipment workload analyzer may include determining the types of various copying, faxing and multi-function machines deployed in the center and how the devices may be grouped, the types of activities that each of the machines may perform, the time periods for which the characteristics may be determined, and the sources from which information about the activities performed by the machines may be collected or received.

Figure 4:
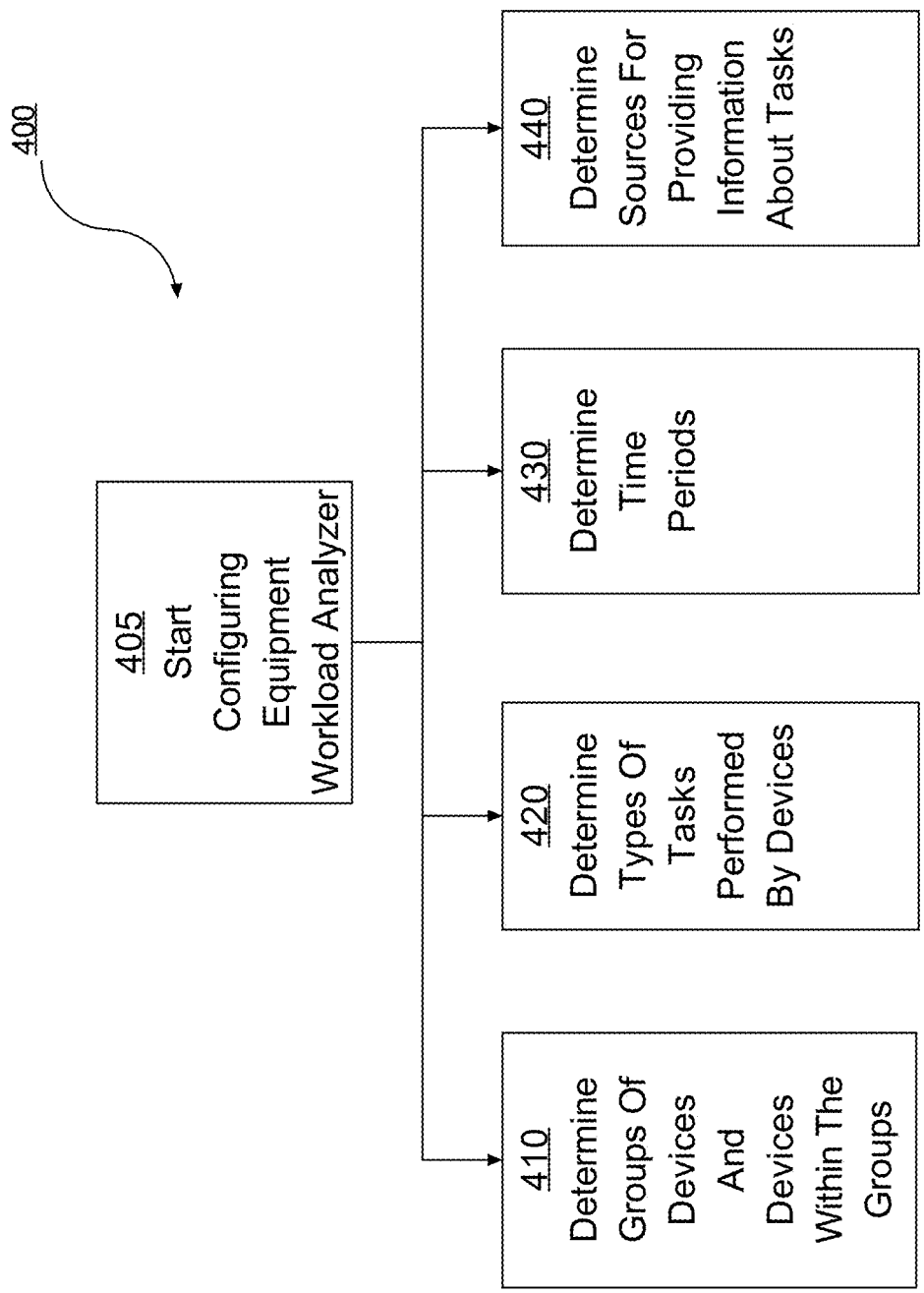
FIG. 4 illustrates an embodiment of a process for configuring an equipment workload analyzer.

FIG. 4 illustrates an embodiment of a process for configuring an equipment workload analyzer. The illustrated embodiment may be applicable to a variety of service applications, including medical applications and other customer-service-providing applications.

In step 405, a process of configuring an equipment workload analyzer starts. This step may include launching a software application or a plugin, generating data objects, instances and other data structures used by the application to instantiate the equipment workload analyzer.

In step 410, one or more groups of devices deployed in a service facility and individual devices in each of the groups of devices are identified. A group of devices may include one or more devices of the same type, the same model or the same utility. The grouping may be performed in a variety of ways. For example, in some implementations, all hematology analyzers may be grouped in one group, when in other implementations hematology analyzers may be grouped based on the name of the manufacturer that manufactured the particular analyzer.

In step 420, the types of activities that each individual device and each of the group of devices are determined. For example, in medical applications, for each hematology analyzer the test identifiers of the tests that the analyzers perform may be identified, and whether some of the tests may be performed on the same accessions of specimens.

In step 430, the time intervals and time periods for collecting activity measures and providing workload and spare capacity characteristics are determined. For example, it may be determined that the measures are to be collected daily, and the characteristics are to be computed for each one-hour-long time interval within a 24-hour-long time period.

It may be assumed that a time period is divided into one or more time intervals. For example, a 24-hour-long time period may be divided into one-hour-long time intervals. The time intervals and periods may be one-hour-long, one-day-long, one-week-long, one-month-long, one-year-long, and so forth.

In step 440, one or more sources configured to provide information about the activities performed by devices of a service facility are determined. For example, in medical applications, one source capable of providing activity measures data may be a LIS. Another source may a database that is accessible to an equipment workload analyzer and that is updated by a processor or a technician who manually enters data into the database. Other sources may include computer workstations or computerized medical devices, configured to automatically download the information about the activities to the database of the equipment workload analyzer. The activity information may include information about various activity measures.

Referring again to FIG. 3, in step 310, one or more activity measures are received for one or more individual devices or groups of devices. The activity measures provide various types of information about the activities performed by the devices deployed in a service facility. For example, in copy-center implementations, the activity measures for a group of copy machines may include daily logs of copy-jobs performed by the copy machines. The logs may include information about the types of the copy-jobs performed during the day, week or month, counts of pages generated for each job, information about special instructions associated with the copy-jobs, and the like.

In step 320, the activity measures are transformed into counts of activities performed by one or more individual devices or groups of devices. The process of transforming the activity measures depends on the type of the activity measure and the method used to identify the activities. The counts may be determined for groups of activities that each of the devices in the device group performed. The counts may also be determined for all activities performed by all devices in the device group. Furthermore, the counts may be determined for each of the device in the group of the devices.

In an embodiment, a count of activities performed by a particular device in a group is determined using the approach described in FIG. 2. Referring again to FIG. 2, if a particular group of devices comprises a device LH1, and the log entries in a LIS report for a particular day indicate that four entries 210-216 have been made for LH1, then a count of activities performed by LH1 on the particular day may be computed from the entries 210-216. As explained for FIG. 2, the entries 210-216 indicate that two accessions were used to perform two tests, and each of the accessions was used to perform two tests. Hence, the count of tests performed by LH1 is four.

In an embodiment, a count of activities performed by a particular device or a group of devices is determined using activities identifiers. A activity identifier may be selected in such a way that it uniquely identifies each individual activity performed by a device. A activity identifier may be unique for each activity and for each device. For example, a activity identifier may be created by concatenating an identifier of a user for whom the activity is performed with a timestamp recorded at the time the order from the user was received. If activity identifiers are used, then determining a count of activities performed by a group of devices may include determining a count of all entries in a LIS log that contain unique activity identifiers.

In an embodiment, a count of activity measures is computed from sub-counts computed for various time intervals. For example, a count may be computed from the sub-count values computed for each day of a week, or each day of a month. Hence, the count may be expressed as a $25^{th}$ percentile, $50^{th}$ percentile, $75^{th}$ percentile, $90^{th}$ percentile, $95^{th}$ percentile, and so forth. For example, a count having a count value "A" and expressed as a $95^{th}$ percentile may indicate that 95% of the days within the certain time period had the count value of "A" or lower. Hence, if counts are expressed as $95^{th}$ percentiles, then computing workspace and spare characteristics refers to $95^{th}$ percentile values. For example, if a group of analyzers includes three analyzers, a peak value for each analyzer is 118, and workload characteristics corresponding to the $95^{th}$ percentile values are 118, 11 and 0, respectively, then a spare capacity may be computed as a difference between the total capacity of all analyzers (118*3) and the sum of counts of workload measures determined for each of the analyzers (118+11+0). This may be expressed as (118*3)−(118+11+0)=225. In this example, the computations were performed using values of workload characteristics corresponding to $95^{th}$ percentile values determined from sub-count values.

In step 330, one or more peak values for a group of devices are obtained or otherwise retrieved. A peak value is a value used by an equipment workload analyzer to determine a relationship between a count of activity measures determined for a device or a group of devices and the peak value. The equipment workload analyzer may compare a peak value with a count of activities to determine whether the count is less than the peak value, equal to the peak value, or greater than the peak value. If the count of measures for a particular activity performed by a particular device or a group of devices is less than the peak value, then it may be concluded that the particular device or the group is underutilized. If the count of measures is equal to the peak value, then it may be concluded that the particular device or the group works at its full capacity.

A peak value may be retrieved from a database associated with an equipment workload analyzer or from any other source communicatively coupled with the equipment workload analyzer.

In an embodiment, peak values may be customized and depend on the nature of the activities for which the thresholds are intended. Peak values may be determined based on the specifications provided by the manufacturers of the devices. For example, a peak value for a copy machine may be suggested by the machine's manufacturer and determined based on such factors as resistance of the machine to overheating, and the like.

In step 340, for each count of the counts determined in step 330, a determination is made whether the count is less than a respective peak value. If a particular count of activity measures for a particular device or a group of devices is less than a respective peak count, then an equipment workload analyzer may determine that the particular device or group is not fully utilized, and thus has some spare capacity. For example, if a particular group of hematology analyzers performed 78 tests on a particular date, but the peak value was determined to be 100, then the equipment workload analyzer may determine that the particular group was underutilized and thus has some spare capacity.

In an embodiment, a particular count of activity measures for a particular device or a group of devices may be equal to a respective peak value. If the count is equal to the peak value, then an equipment workload analyzer may conclude that workload of the particular device or group matches the recommended workload level, and thus the particular device or group has no spare capacity.

In an embodiment, a count of activity measures for a particular device or a group of devices may be greater than a respective peak value. This may indicate that the device or the group is utilized above the recommended workload peak. However, this may or may not indicate that the device or the group is over utilized. For example, if the peak value was set below a workload level recommended by a manufacturer, then it may be acceptable for the count of activity measure to exceed the peak value. In such a situation, the count may be compared with an additional peak value, such as a maximum workload level peak, to determine whether the situation presents a problem.

If in step 350 a determination is made that a particular count is less than a respective peak value, then the process proceeds to step 360; otherwise the process proceeds to step 370.

In step 360, an equipment workload analyzer generates a report including an indication of spare workload capacity that exists on a particular device or a group of devices.

A report may be provided in a variety of forms, including a message, an electronic email with an attachment, a graph, a plot, an interactive display or the like. A report may be sent electronically or displayed on a user interface generated for a user. For example, a report may be generated as a PDF file and the PDF file may include a graph indicating time periods during which a particular device or a particular group of devices had some spare capacity. A report may also depict one or more workload characteristics for the particular device or the group. The characteristics may be plotted against a time axis. Furthermore, a report may depict numerical values of the workload characteristics and spare capacity characteristics plotted against the time axis. Examples of various reports are provided below.

In step 370, an equipment workload analyzer generates a report including an indication that spare capacity is unavailable on a particular device or a group of devices. As in step 360, a report may be provided in a variety of forms, including a message, an electronic email with an attachment, a graph, a plot, an interactive display or the like. A report may include indications of the time periods or days during which a particular device or a group of devices has no spare capacity. Those time periods or days may be highlighted or otherwise marked to draw attention to them.

In an embodiment, a report comprises one or more workload characteristics of a service facility. The workload characteristics may be determined based on the activity measures and counts obtained for the activity measures. The workload characteristics may be determined for a particular time period, for a particular activity, or a particular group of activities. For example, based on the counts of activity measures for each of the analyzers in a group of analyzers, workload characteristics may be determined for each of the devices and graphically represented in a report. The graphs may indicate which of the devices are underutilized, which devices are operating at their full capacity.

The process recited in steps 300-360 may be repeated by an equipment workload analyzer according to a scheduler or upon receiving a request. For example, the process may be repeated on a daily basis and generated reports may be provided to a management of a service facility daily. The process may also be repeated weekly or on a monthly basis. Furthermore, the process may be repeated each time a request for the report is received. For example, a report may be requested when the management of a service facility is considering purchasing some new equipment or upgrading some of the already deployed equipment. The report may provide indications of the type of devices that may be retired or upgraded.

5.0 Types of Reports

Once counts of activity measures are determined, the count information may be processed and used to determine workload (throughput) and spare capacity characteristics of a service facility. Based on the workload and spare capacity characteristics, one or more reports may be generated and provided to users. The reports may be provided automatically, periodically or upon receiving a request. A request may specify the types of the requested reports, and the forms in which the requested reports are to be provided.

The reports may be customized in a variety of ways. For example, some reports may provide just workload information; other reports may provide just spare capacity characteristics; other reports may provide both types of characteristics.

The reports may be customized in a variety of ways. Customization of a report may include specifying the type of information that is requested and the time intervals for which the information is requested. For example, reports pertaining to workload and spare capacity characteristics may be customized to provide information graphically depicting workload characteristics plotted against time intervals indicated by a time axis. Other reports may be customized to provide information organized in spreadsheets or tables; portions of the tables may be highlighted to indicate the time intervals during which some spare capacity is available on certain devices or groups of devices.

In an embodiment, reports may be customized for each week of the month or the year. For example, the workload and spare capacity characteristics may be represented in such a way that the days that correspond to holidays are not indicated as days when some spare capacity is available.

The reports may also be customized for each month of the upcoming years. This type of customization is useful if a service facility is planning to purchase new equipment, or retire or upgrade some of the equipment. For example, if a service facility is growing and expanding, then by analyzing the workload and spare capacity characteristics, the management of the facility may determine the type of equipment to be retired, upgraded or purchased. If a service facility is deploying some additional equipment, then by analyzing the workload and spare capacity characteristics, the management may be able to estimate throughput of the new configuration of the devices.

7.0 Examples of Reports

Figure 5:
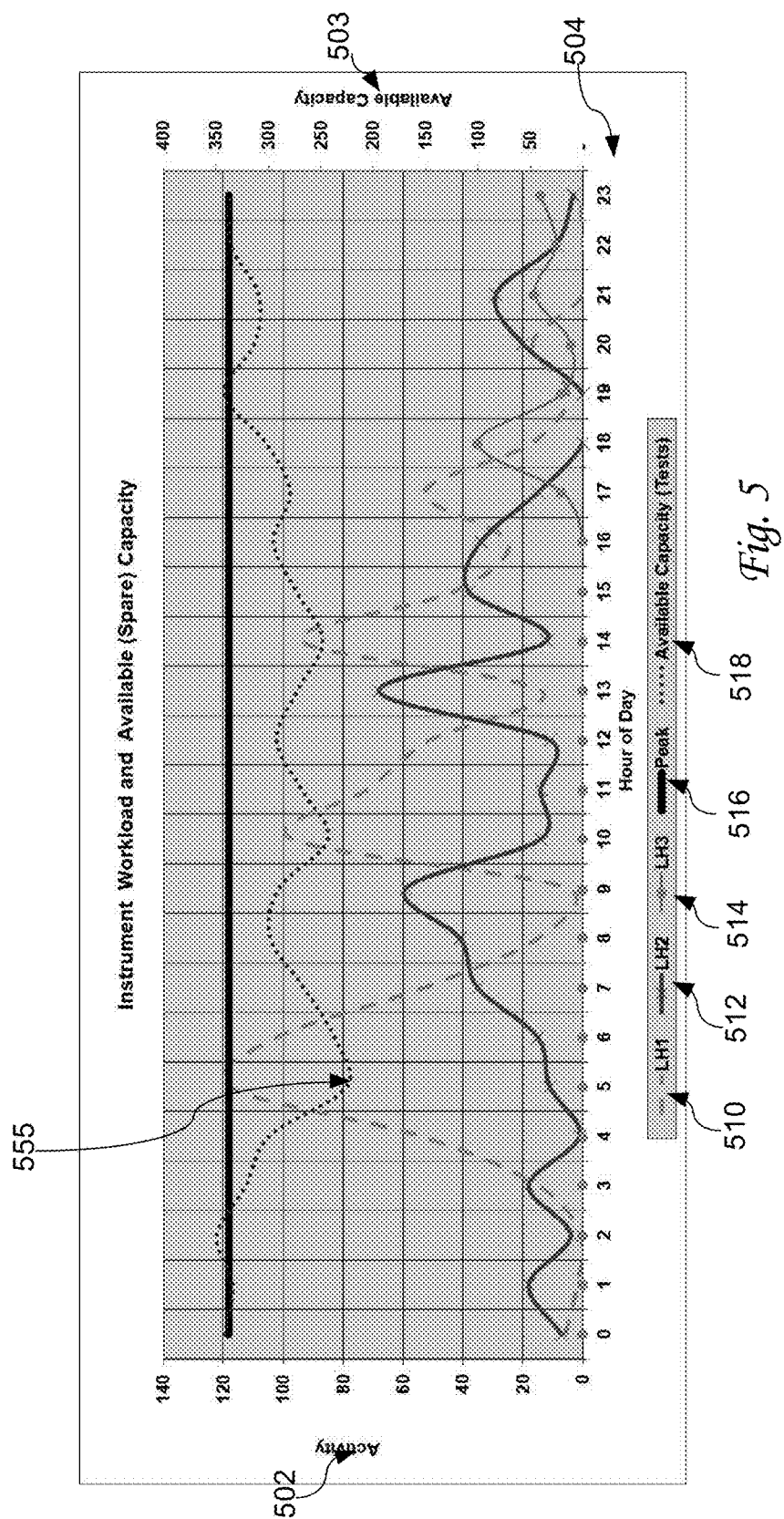
FIG. 5 illustrates an embodiment of a report to depict the instrument workload and spare capacity of the instruments deployed in a medical facility.

FIG. 5 illustrates an embodiment of a report to depict the instrument workload and spare capacity of the instruments deployed in a medical facility. The report depicted in FIG. 5 has a first vertical axis 502 that indicates various counts of activity and a second vertical axis 503 that indicates various counts of available capacity. Horizontal axis 504 indicates a 24-hour-long time period starting at midnight and ending at 11:59 PM of a particular day. The report also depicts five plots, and each of the plots is labeled using a respective label. The plots include a plot of the instrument workload of instrument LH1, indicated using a broken line 510; a plot of the instrument workload of instrument LH2, marked using a continuous line 512; a plot of the instrument workload of instrument LH3, marked using lines and dots 514; a peak capacity plot, marked using a thick continuous line 516; and an available capacity plot, marked using a dotted line 518.

The graphical format of reports shown herein may vary in different embodiments. For example, the particular forms of symbols, broken lines, solid lines, and other graphical elements are not critical and may be varied in different embodiments. The scale, endpoints, and location of axes also may vary in different embodiments.

A plot of the instrument workload of instrument LH1 indicates that instrument LH1 was working at its peak capacity at about 5 AM. The workload of instrument LH1 was also rather heavy at 10 AM, 2 PM and 5 PM. The workload of instrument LH2 was moderate and reached its peaks at about 9 AM and 1 PM. The workload of instrument LH3 was rather light, and reached its peak at about 6 PM. The peak capacity of the instruments LH1-LH3 is depicted using marking 516. The plot indicating the available capacity (marked using a dotted line 518) is obtained by processing the data provided by the plots 510-516 and the previous 6 days. For example, since almost all instruments LH1-LH2 were idle at 2 AM, 7 PM and 11 PM, the spare capacity plot reaches its high points at 2 PM, 7 PM and 11 PM. In contrast, since at least instrument LH1 was utilized at its top capacity at about 5 AM, the spare capacity plot reaches its low point at about 5 AM.

Spare capacity characteristics may be computed using various approaches. For example, a spare capacity value for a particular time interval may be computed from workload values obtained for the devices for the particular time interval and a peak value.

This may be illustrated using the following example: if a service facility deployed three hematology analyzers LH1, LH2 and LH3, and the maximum number of specimens that each individual hematology analyzer may process is 118, but during a particular time interval, the analyzers actually processed 118, 11 and 0 specimens, respectively, then the spare capacity of the group of the three analyzers may be expressed as a difference between the total maximum number of specimens that the analyzers could have processed during the particular time interval and the total actual number of specimens that the analyzers actually processed. The difference may be expressed as follows: (118*3)−(118+11+0)=354−129=225. Therefore, the spare capacity characteristics of the group of the analyzers indicate that the analyzers had the ability to process additional 225 specimens during the particular time interval. This value is shown in FIG. 5 using a pointer 555, which indicates that the available spare capacity of the devices at 5 AM is 225, which may be verified on the second vertical axis 503.

In an embodiment, counts of tests are expressed as percentile values. If a workload value corresponds to $95^{th}$ percentile, that that means that 95% of hours within a certain time period (such as one week) had the particular workload value or lower. Hence, if for the one week period, the $95^{th}$ percentile workload value for all three analyzers was 118, then the spare capacity for $95^{th}$ workload percentile for the group of devices of LH1, LH2 and LH3 may be computed as (118*3)−(118+11+0)=225. If instead of $95^{th}$ percentile values, $98^{th}$ percentile values are used, the spare capacity computed in this case may be higher.

Figure 6:
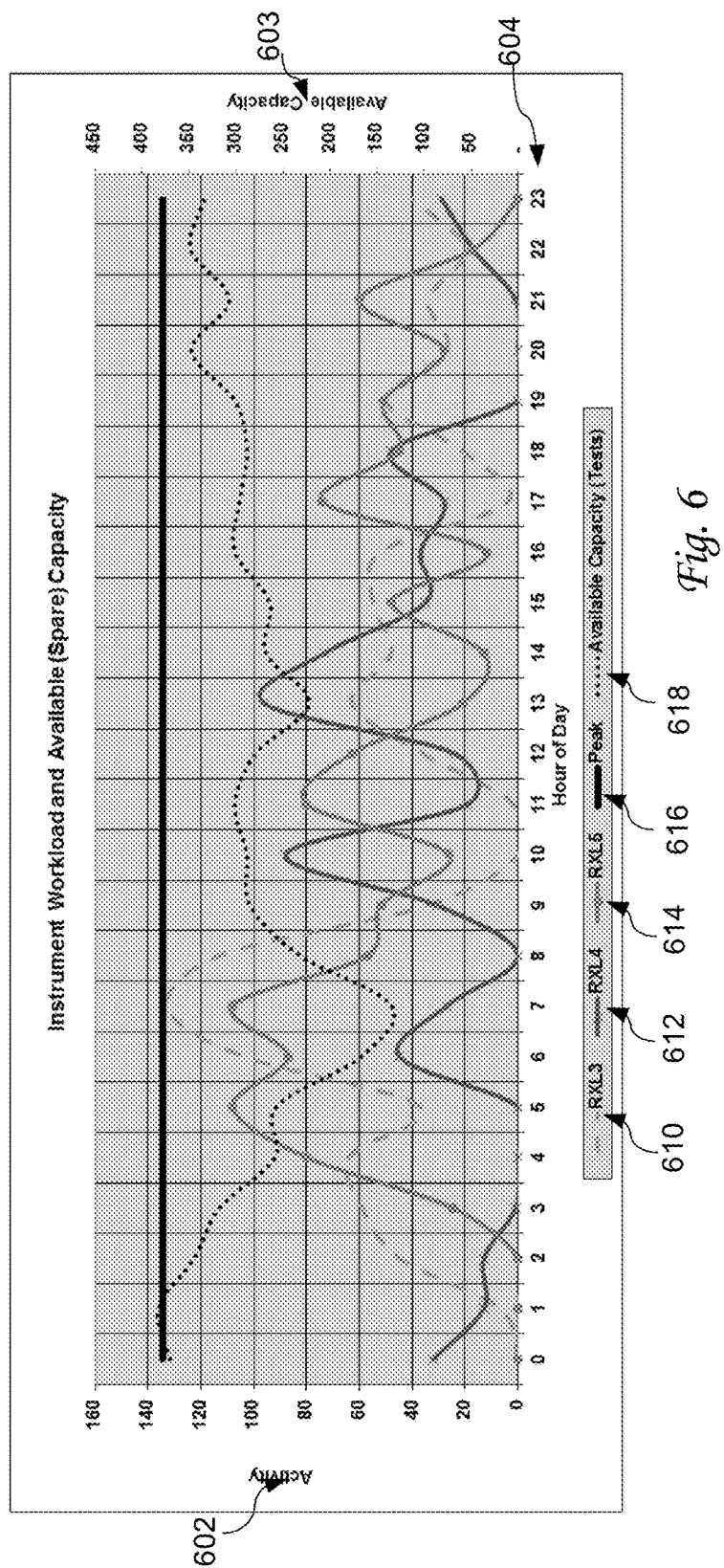
FIG. 6 illustrates an embodiment of a report to depict the instrument workload and spare capacity of the instruments deployed in a medical facility.

FIG. 6 illustrates an embodiment of a report to depict the instrument workload and spare capacity of the instruments deployed in a medical facility. The report depicted in FIG. 6 has a first vertical axis 602 that indicates various counts of activities and a second vertical axis 603 that indicates various counts of available spare capacity. Horizontal axis 604 indicates a 24-hour-long time period starting at midnight and ending at 11:59 PM of a particular day. The report also depicts five plots, and each of the plots is labeled using a respective label. The plots include a plot of the instrument workload of instrument RXL3, indicated using a broken line 610; a plot of the instrument workload of instrument RXL4, marked using a continuous line 612; a plot of the instrument workload of instrument RXL5, marked using lines and dots 614; a peak capacity plot, marked using a thick continuous line 616; and an available capacity plot, marked using a dotted line 618.

The graphical format of the report shown herein may vary in different embodiments. For example, the particular forms of symbols, broken lines, solid lines, and other graphical elements are not critical and may be varied in different embodiments. The scale, endpoints, and location of axes also may vary in different embodiments.

A plot of the instrument workload of instrument RXL3 indicates that instrument RXL3 was working at its peak capacity at about 7 AM. The workload of instrument RXL4 was moderate and reached its peaks at about 10 AM and 1 PM. The workload of instrument RXL5 was rather heavy, and reached its peak at about 5 AM and 7 AM. The peak capacity of the instruments RXL3-RXL5 is depicted using marking 516. The plot indicating the available capacity (marked using a dotted line 518) was obtained by processing the data provided by the plots 610-616 and the prior 6 days. For example, since almost all instruments RXL3-RXL4 were idle at about 1 AM, the spare capacity plot reaches its high points at 1 AM. In contrast, since at least instrument RXL3 was utilized at its top capacity at about 7 AM, the spare capacity plot reaches its low point at about 7 AM.

The ability to determine instrument spare characteristics for a service facility may provide a variety of benefits to the facility. For example, it may assist in developing a business-model for the facility, and help in business planning. It may also help in making business decisions, such as equipment purchase decisions. It may also be helpful in managing a variety of services that the service facility provides to the public. A manager of such a service facility may want to request workload and spare capacity reports customized for various time periods, devices and group of the devices to determine whether the facility has the capacity for providing additional services.

6.0 IMPLEMENTATION MECHANISMS—HARDWARE OVERVIEW

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

Figure 7:
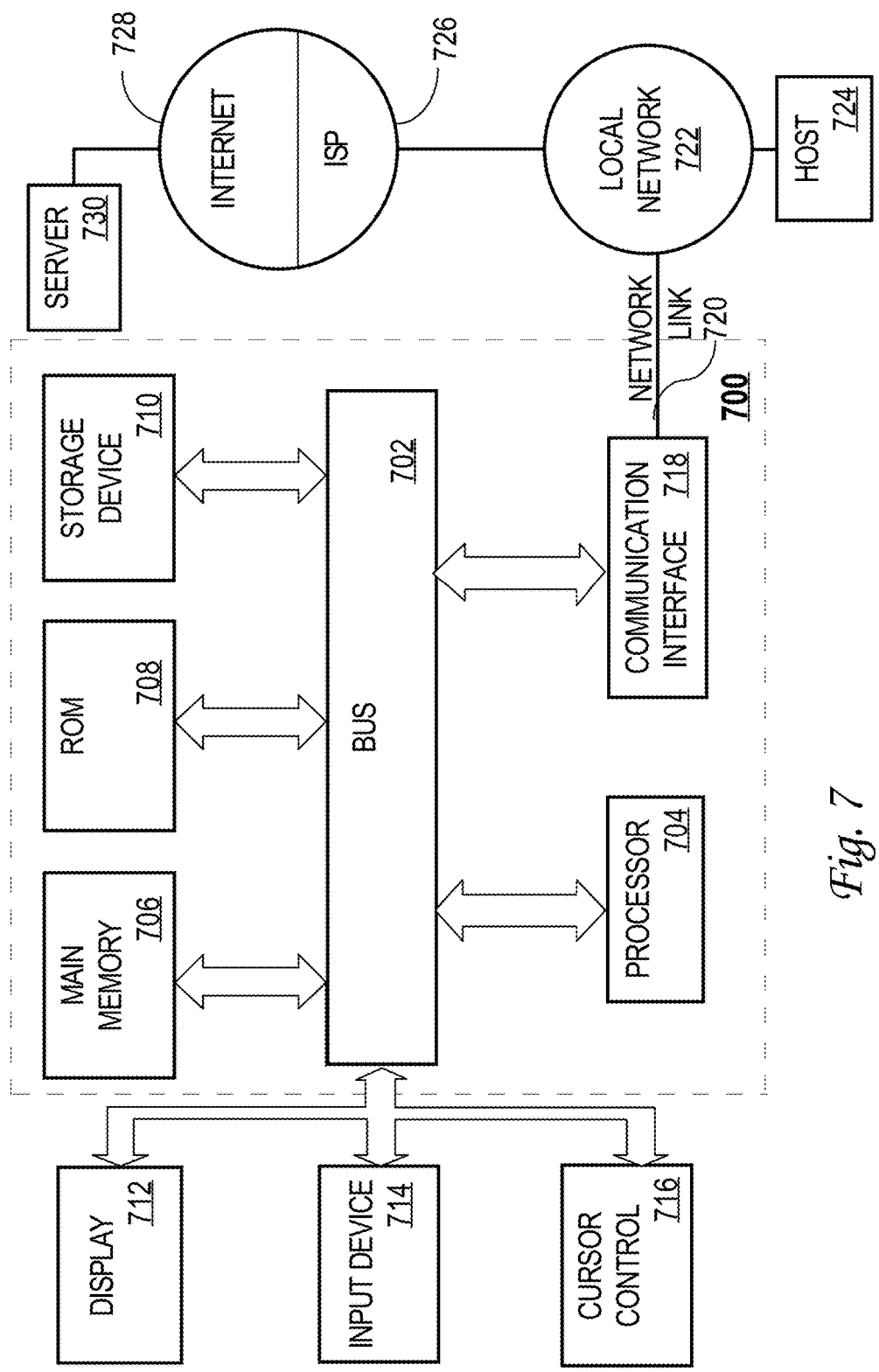
FIG. 7 illustrates an example computer system with which an embodiment may be implemented.

For example, FIG. 7 is a block diagram that illustrates a computer system 700 upon which an embodiment of the invention may be implemented. Computer system 700 includes a bus 702 or other communication mechanism for communicating information, and a hardware processor 704 coupled with bus 702 for processing information. Hardware processor 704 may be, for example, a general purpose microprocessor.

Computer system 700 also includes a main memory 706, such as a random access memory (RAM) or other dynamic storage device, coupled to bus 702 for storing information and instructions to be executed by processor 704. Main memory 706 also may be used for storing temporary variables or other intermediate information during execution of instructions to be executed by processor 704. Such instructions, when stored in non-transitory storage media accessible to processor 704, render computer system 700 into a special-purpose machine that is customized to perform the operations specified in the instructions.

Computer system 700 further includes a read only memory (ROM) 708 or other static storage device coupled to bus 702 for storing static information and instructions for processor 704. A storage device 710, such as a magnetic disk or optical disk, is provided and coupled to bus 702 for storing information and instructions.

Computer system 700 may be coupled via bus 702 to a display 712, such as a cathode ray tube (LCD, CRT), for displaying information to a computer user. An input device 714, including alphanumeric and other keys, is coupled to bus 702 for communicating information and command selections to processor 704. Another type of user input device is cursor control 716, such as a mouse, a trackball, or cursor direction keys for communicating direction information and command selections to processor 704 and for controlling cursor movement on display 712. This input device typically has two degrees of freedom in two axes, a first axis (e.g., x) and a second axis (e.g., y), that allows the device to specify positions in a plane.

Computer system 700 may implement the techniques described herein using customized hard-wired logic, one or more ASICs or FPGAs, firmware and/or program logic which in combination with the computer system causes or programs computer system 700 to be a special-purpose machine. According to one embodiment, the techniques herein are performed by computer system 700 in response to processor 704 executing one or more sequences of one or more instructions contained in main memory 706. Such instructions may be read into main memory 706 from another storage medium, such as storage device 710. Execution of the sequences of instructions contained in main memory 706 causes processor 704 to perform the process steps described herein. In alternative embodiments, hard-wired circuitry may be used in place of or in combination with software instructions.

The term "storage media" as used herein refers to any non-transitory media that store data and/or instructions that cause a machine to operation in a specific fashion. Such storage media may comprise non-volatile media and/or volatile media. Non-volatile media includes, for example, optical or magnetic disks, such as storage device 710. Volatile media includes dynamic memory, such as main memory 706. Common forms of storage media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 702. Transmission media can also take the form of acoustic or light waves, such as those generated during radio-wave and infra-red data communications.

Various forms of media may be involved in carrying one or more sequences of one or more instructions to processor 704 for execution. For example, the instructions may initially be carried on a magnetic disk or solid state drive of a remote computer. The remote computer can load the instructions into its dynamic memory and send the instructions over a telephone line using a modem. A modem local to computer system 700 can receive the data on the telephone line and use an infra-red transmitter to convert the data to an infra-red signal. An infra-red detector can receive the data carried in the infra-red signal and appropriate circuitry can place the data on bus 702. Bus 702 carries the data to main memory 706, from which processor 704 retrieves and executes the instructions. The instructions received by main memory 706 may optionally be stored on storage device 710 either before or after execution by processor 704.

Computer system 700 also includes a communication interface 718 coupled to bus 702. Communication interface 718 provides a two-way data communication coupling to a network link 720 that is connected to a local network 722. For example, communication interface 718 may be an integrated services digital network (ISDN) card, cable modem, satellite modem, or a modem to provide a data communication connection to a corresponding type of telephone line. As another example, communication interface 718 may be a local area network (LAN) card to provide a data communication connection to a compatible LAN. Wireless links may also be implemented. In any such implementation, communication interface 718 sends and receives electrical, electromagnetic or optical signals that carry digital data streams representing various types of information.

Network link 720 typically provides data communication through one or more networks to other data devices. For example, network link 720 may provide a connection through local network 722 to a host computer 724 or to data equipment operated by an Internet Service Provider (ISP) 726. ISP 726 in turn provides data communication services through the world wide packet data communication network now commonly referred to as the "Internet" 728. Local network 722 and Internet 728 both use electrical, electromagnetic or optical signals that carry digital data streams. The signals through the various networks and the signals on network link 720 and through communication interface 718, which carry the digital data to and from computer system 700, are example forms of transmission media.

Computer system 700 can send messages and receive data, including program code, through the network(s), network link 720 and communication interface 718. In the Internet example, a server 730 might transmit a requested code for an application program through Internet 728, ISP 726, local network 722 and communication interface 718.

The received code may be executed by processor 704 as it is received, and/or stored in storage device 710, or other non-volatile storage for later execution.

In the foregoing specification, embodiments of the invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

7.0 EXTENSIONS AND ALTERNATIVES

In the foregoing specification, embodiments of the invention have been described with reference to numerous specific details that may vary from implementation to implementation. The specification and drawings are, accordingly, to be regarded in an illustrative rather than a restrictive sense.

What is claimed is:

1. A method, comprising:
    retrieving, without direct observation, one or more activity measures recorded within a particular time period and associated with activities performed by a group of devices in a service facility, wherein the recorded one or more activity measures represent an incomplete information about activities performed by the group of devices;
    transforming the one or more activity measures, the transforming comprising:
        processing the incomplete information about the activities performed by the group of devices to obtain detailed information about the activities performed by the group of devices; and
        processing the detailed information about the activities performed by the group of devices to obtain a count of activities performed by the group of devices within the particular time period;
    determining whether the count of activities for the group of devices is less than a peak value for the group of devices; and
    in response to determining that the count of activities for the group of devices is less than a specified value for the group of devices:
        determining a spare capacity value for the group of devices for the particular time period as a difference between the specified value and the count of activities for the group of devices; and
        causing generating a first display of the spare capacity value for the group of devices on a computer display unit;
    wherein the method is performed by one or more computing devices.

2. The method of claim 1, wherein the transforming the one or more activity measures further comprises incrementing the count of activities for each instance of a activity measure, of the one or more activity measures, that has been recorded in a computer information system for any device of the group of devices within the particular time period.

3. The method of claim 1, further comprising:
    transforming the one or more activity measures into one or more individual counts of activities performed by one or more devices of the group of devices within the particular time period; and
    for each individual count of activities of the one or more individual counts, determining whether the individual count of activities for a device of the one or more devices is less than an individual peak value for the device, and in response thereto:
        determining an individual spare capacity value for the device for the particular time period as a change between the individual peak value for the device and the individual count of activities for the device; and
        causing generating a second display of the individual spare capacity value for the device on the computer display unit.

4. The method of claim 3, wherein the transforming the one or more activity measures further comprises incrementing, for each device, the individual count of activities for each instance of a activity measure, of the one or more activity measures, that has been recorded in a laboratory information system for the device of the group of devices within the particular time period.

5. The method of claim 3, further comprising determining, based on the one or more individual counts determined for the one or more devices, which of the one or more devices performs at a peak capacity during the particular time period.

6. The method of claim 3, further comprising determining, based on the one or more individual counts determined for the one or more devices, a particular time sub-period, within the particular time period, at which the group of devices performs at a peak capacity.

7. The method of claim 1, wherein the activities comprise any one of: processing a specimen collection, processing a specimen accession, performing a test on the specimen accession, or obtaining results for the test performed on the specimen accession.

8. The method of claim 1, comprising receiving the one or more activity measures from an activity log of a laboratory information system.

9. The method of claim 1, comprising causing generating any one of: a graphical user interface on a computer display comprising an indication whether the spare capacity value for the group of devices is available, or an electronic message indicating whether the spare capacity value for the group of devices is available and sending the electronic message to a user.

10. The method of claim 9, comprising causing generating indications of: a activity throughput for each device of the group of devices, a combined peak throughput for the group of devices, an available capacity for each device of the group of devices.

11. A non-transitory computer-readable storage medium storing one or more sequences of instructions which, when executed, cause performance of steps comprising:
retrieving, without direct observation, one or more activity measures recorded within a particular time period and associated with activities performed by a group of devices in a service facility, wherein the recorded one or more activity measures represent an incomplete information about activities performed by the groups of devices;
transforming the one or more activity measures, the transforming comprising:
processing the incomplete information about the activities performed by the group of devices to obtain detailed information about the activities performed by the group of devices; and
processing the detailed information about the activities performed by the group of devices to obtain a count of activities performed by the group of devices within the particular time period;
determining whether the count of activities for the group of devices is less than a peak value for the group of devices; and
in response to determining that the count of activities for the group of devices is less than the peak value for the group of devices:
determining a spare capacity value for the group of devices for the particular time period as a difference between a specified value and the count of activities for the group of devices; and
causing generating a first display of the spare capacity value for the group of devices on a computer display unit.

12. The non-transitory computer-readable storage medium of claim 11, wherein the instructions that cause performance of the transforming the one or more activity measures further comprise additional instruction which, when executed cause incrementing the count of activities for each instance of a activity measure, of the one or more activity measures, that has been recorded in a computer information system for any device of the group of devices within the particular time period.

13. The non-transitory computer-readable storage medium of claim 11, further comprising additional instructions which, when executed, cause:
transforming the one or more activity measures into one or more individual counts of activities performed by one or more devices of the group of devices within the particular time period; and
for each individual count of activities of the one or more individual counts, determining whether the individual count of activities for a device of the one or more devices is less than an individual peak value for the device, and in response thereto:
determining an individual spare capacity value for the device for the particular time period as a change between the individual peak value for the device and the individual count of activities for the device; and
causing generating a second display of the individual spare capacity value for the device on the computer display unit.

14. The non-transitory computer-readable storage medium of claim 13, wherein the instructions that cause performance of the transforming the one or more activity measures further comprise additional instructions which, when executed, cause incrementing, for each device, the individual count of activities for each instance of a activity measure, of the one or more activity measures, that has been recorded in a laboratory information system for the device of the group of devices within the particular time period.

15. The non-transitory computer-readable storage medium of claim 13, further comprising additional instructions which, when executed, cause determining, based on the one or more individual counts determined for the one or more devices, which of the one or more devices performs at a peak capacity during the particular time period.

16. The non-transitory computer-readable storage medium of claim 13, further comprising additional instructions which, when executed, cause determining, based on the one or more individual counts determined for the one or more devices, a particular time sub-period, within the particular time period, at which the group of devices performs at a peak capacity.

17. The non-transitory computer-readable storage medium of claim 11, wherein the activities comprise any one of: processing a specimen collection, processing a specimen accession, performing a test on the specimen accession, or obtaining results for the test performed on the specimen accession.

18. The non-transitory computer-readable storage medium of claim 11, comprising additional instructions which, when executed, cause receiving the one or more activity measures from an activity log of a laboratory information system.

19. The non-transitory computer-readable storage medium of claim 11, comprising additional instructions which, when executed, cause generating any one of: a graphical user interface on a computer display comprising an indication whether the spare capacity value for the group of devices is available, or an electronic message indicating whether the spare capacity value for the group of devices is available and sending the electronic message to a user.

20. The non-transitory computer-readable storage medium of claim 19, comprising additional instructions which, when executed, cause generating indications of: a activity throughput for each device of the group of devices, a combined peak throughput for the group of devices, an available capacity for each device of the group of devices.

* * * * *